US012805708B2

(12) United States Patent
Keshtgar et al.

(10) Patent No.: US 12,805,708 B2
(45) Date of Patent: Nov. 24, 2026

(54) SYSTEMS AND METHODS FOR ROBOTIC ENDOSCOPE SHAFT

(71) Applicant: Noah Medical Corporation, San Carlos, CA (US)

(72) Inventors: Maziyar Keshtgar, San Jose, CA (US); Hazim Amir, San Jose, CA (US)

(73) Assignee: Noah Medical Corporation, San Carlos, CA (US)

( * ) Notice: Subject to any disclaimer, the term of this patent is extended or adjusted under 35 U.S.C. 154(b) by 47 days.

(21) Appl. No.: 18/652,983

(22) Filed: May 2, 2024

(65) Prior Publication Data

US 2024/0277216 A1 Aug. 22, 2024

Related U.S. Application Data

(63) Continuation of application No. PCT/US2022/053730, filed on Dec. 21, 2022.

(60) Provisional application No. 63/373,800, filed on Aug. 29, 2022, provisional application No. 63/294,304, filed on Dec. 28, 2021.

(51) Int. Cl.
*A61B 1/008* (2006.01)
*A61B 1/005* (2006.01)

(52) U.S. Cl.
CPC ............ *A61B 1/008* (2013.01); *A61B 1/0052* (2013.01)

(58) Field of Classification Search
CPC ...................................................... A61B 1/008
USPC .......................................................... 600/141
See application file for complete search history.

(56) References Cited

U.S. PATENT DOCUMENTS

2006/0189897 A1* 8/2006 Poncet .............. A61M 25/0045 600/585
2010/0168519 A1* 7/2010 Matsuo .............. A61B 1/00078 600/139
2019/0247622 A1* 8/2019 Romano ............... A61M 25/09
2021/0361364 A1 11/2021 Al-Jadda et al.
2021/0393111 A1* 12/2021 Do ....................... A61B 1/0055

FOREIGN PATENT DOCUMENTS

WO WO-2012073072 A1 * 6/2012 ............. A61B 1/307
WO WO-2021127449 A1 * 6/2021 ........... A61B 1/0055

OTHER PUBLICATIONS

PCT/US2022/054101 International Preliminary Report on Patentability dated Mar. 27, 2023.
EP22917236.6 Extended European Search Report dated Nov. 19, 2025.

* cited by examiner

*Primary Examiner* — Yulin Sun
(74) *Attorney, Agent, or Firm* — Wilson Sonsini Goodrich & Rosati

(57) ABSTRACT

An articulating flexible endoscope is provided. The articulating flexible endoscope comprising: an elongated member extending between a distal end and a proximal end, the elongated member comprising: an active bending section steerable by one or more pull wires; and a passive section located between the active bending section and a proximal shaft section, wherein the passive section comprises an anti-prolapse structure that defines a minimum bend radius of the passive section.

16 Claims, 18 Drawing Sheets

210

200

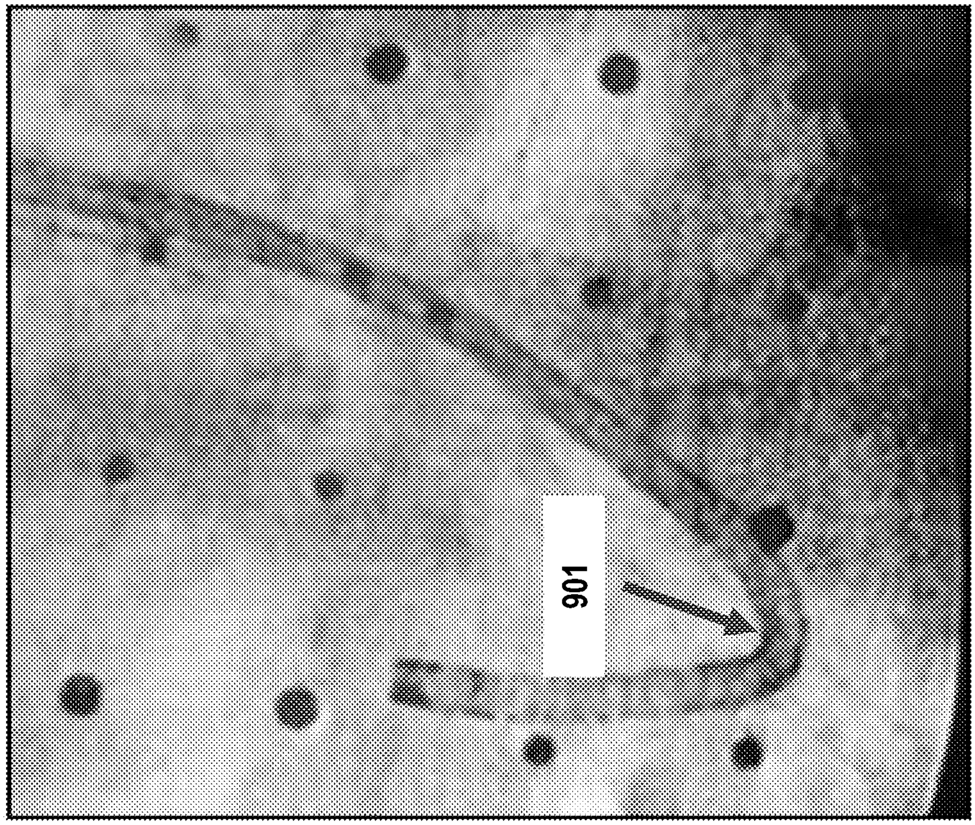
FIG. 9
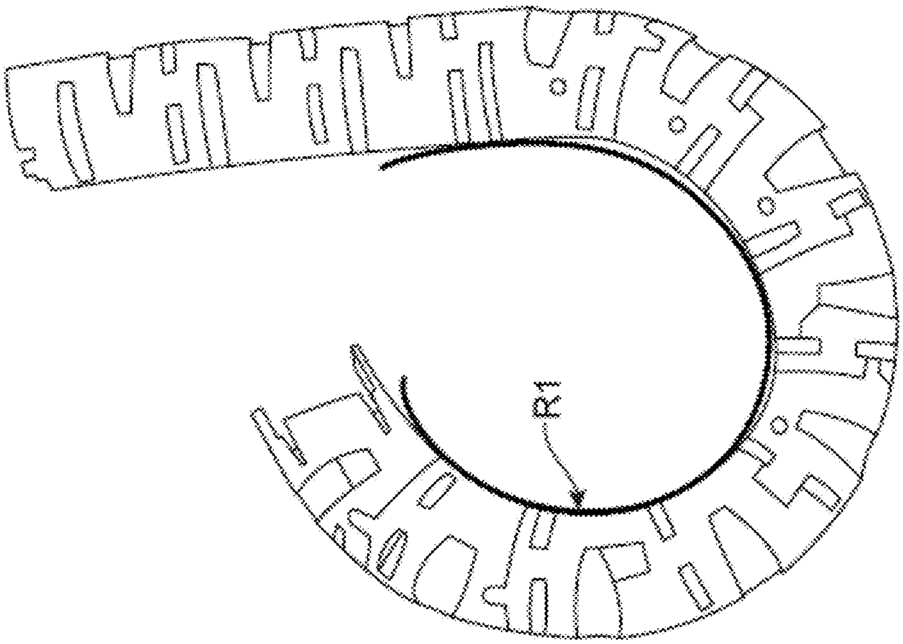

SYSTEMS AND METHODS FOR ROBOTIC ENDOSCOPE SHAFT

REFERENCE

This application is a continuation of International Application No. PCT/US2022/053730, filed Dec. 21, 2022, which claims priority to U.S. Provisional Patent Application No. 63/294,304, filed on Dec. 28, 2021, and U.S. Provisional Patent Application No. 63/373,800, filed on Aug. 29, 2022, each of which is entirely incorporated herein by reference.

BACKGROUND

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others. For example, flexible bronchoscope may be used for lung cancer diagnosis and/or surgical treatment. However, one challenge in bronchoscopy is reaching the upper lobe of the lung while navigating through the airways. In another example, flexible endoscopy has been used to inspect and treat disorders of the gastrointestinal (GI) tract without the need for creating an opening on the patient's body. The endoscope is introduced via the mouth or anus into the upper or lower GI tracts respectively. A miniature camera at the distal end captures images of the GI wall that help the clinician in their diagnosis of the GI diseases. Simple surgical procedures (like polypectomy and biopsy) can be performed by introducing a flexible tool via a working channel to reach the site of interest at the distal end. As sections of elongate device are curved as they are moved through the one or more passageways, the curved sections are subject to compression. The compression causes the elongate device to bend and contact the walls of one or more passageways along its length. In areas where there are one or more large passageways around the elongate device, when the distal end of the device encounters tissue resistance, the elongate device may bend within the large airway and move towards an unintended region of anatomy and not in the intended direction ("prolapsing"). Prolapsing is more probable when tissue resistance gets higher (e.g., due to airways being too small, lung not fully inflated, diseased tissue, blind insertion, etc.) The prolapse or kink may result in potential damage as it may expose the sharp edges of the kinked elongate device and complicate the surgical procedure.

Endoscopes are traditionally made to be re-usable, which may require thorough cleaning, dis-infection, and/or sterilization after each procedure. In most cases, cleaning, dis-infection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single-use have become popular for instruments that are difficult to clean properly. Single-use, disposable devices may be packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

SUMMARY

Recognized herein is a need for a robotically endoscope that allows for performing surgical procedures or diagnostic operations with improved performance and cost-efficiency. Recognized also herein are devices and systems comprising endoscopes which may be disposable and may not require extensive cleaning procedures. The present disclosure provides low-cost, single-use articulatable endoscope for diagnosis and treatment in various applications such as bronchoscopy, urology, gynecology, arthroscopy, orthopedics, ENT, gastro-intestine endoscopy, neurosurgery, and various others. In some embodiments, the present disclosure provides a single-use, disposable, robotically controlled bronchoscope for use with a robotic system to enable diagnostic evaluation of lesions anywhere in the pulmonary anatomy. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

The present disclosure provides methods and apparatuses that can improve the performance of articulating flexible endoscope when it is navigated through a body cavity. A flexible elongate member may be navigated through an airway/channel with improved anti-prolapse capability. In an aspect of the present disclosure, an articulating flexible endoscope is provided. The endoscope comprises: an elongated member extending between a distal end and a proximal end, the elongated member comprising: an active bending section steerable by one or more pull wires; and a passive section located between the active bending section and a proximal shaft section, where the passive section comprises an anti-prolapse structure that determines a minimum bend radius of the passive section thereby preventing prolapse.

In some embodiments, the distal end is connected to a distal tip portion of the articulating flexible endoscope and wherein the distal tip portion comprises a structure to receive an imaging device, a position sensor, and an illumination device. In some embodiments, the proximal end is connected to a proximal portion of the articulating flexible endoscope and wherein the proximal portion comprises a driving mechanism for applying a force to the one or more pull wires.

In some embodiments, the anti-prolapse structure is integrally formed within the passive section. In some cases, the anti-prolapse structure comprises a cut pattern and the minimum bend radius is determined based at least in part on a gap size of the cut pattern. In some instances, the cut pattern comprises a gap and an interlocking feature.

In some embodiments, the passive section has two or more different minimum bend radii. In some cases, the anti-prolapse structure comprises a cut pattern and the two or more different minimum end radii are determined by selecting different gap sizes and/or selecting different pitches of the cut pattern.

In some embodiments, a minimum bend radius of the active bending section is smaller than the minimum bend radius of the passive section. In some cases, the active bending section has two or more different minimum bend radii.

In some embodiments, the articulating flexible endoscope further comprises one or more coil pipes with a distal end anchored to an interface between the passive section and the active bending section. In some cases, a proximal end of the one or more coil pipes is anchored to a handle of the articulating flexible endoscope. In some embodiments, the articulating flexible endoscope further comprises a jacket as an outer layer of the elongated member. In some cases, the jacket comprises multiple layers and has variable stiffness along a length of the jacket. In some embodiments, the proximal shaft section has a stiffness greater than a stiffness of the passive section.

In another aspect, a method is provided for preventing prolapse or kink for an articulating flexible endoscope. The method comprises: providing an elongated member; navigating the articulating flexible endoscope through a passageway by steering an active bending section of the elongated member via one or more pull wires; and providing a passive section located between the active bending section and a proximal shaft section, where the passive section comprises an anti-prolapse structure that determines a minimum bend radius of the passive section thereby preventing prolapse while the articulating flexible endoscope is navigating through the passageway.

In some embodiments, the anti-prolapse structure is integrally formed within the passive section. In some embodiments, the anti-prolapse structure comprises a cut pattern including repeated gap feature and interlocking feature. In some cases, the minimum bend radius is determined based at least in part on a gap size of the gap feature. In some embodiments, the passive section has two or more different minimum bend radii. In some cases, the anti-prolapse structure comprises a cut pattern and the two or more different minimum end radii are determined by selecting different gap sizes and/or selecting different pitches of the cut pattern.

In some embodiments, the active bending section has a minimum bend radius that is smaller than the minimum bend radius of the passive section. In some embodiments, the active bending section has two or more different minimum bend radii.

It should be noted that the provided modular endoscope components and various components of the device can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 9 shows an example of a bending section with uniform minimum bend radius.

DETAILED DESCRIPTION OF THE INVENTION

Figure 1:
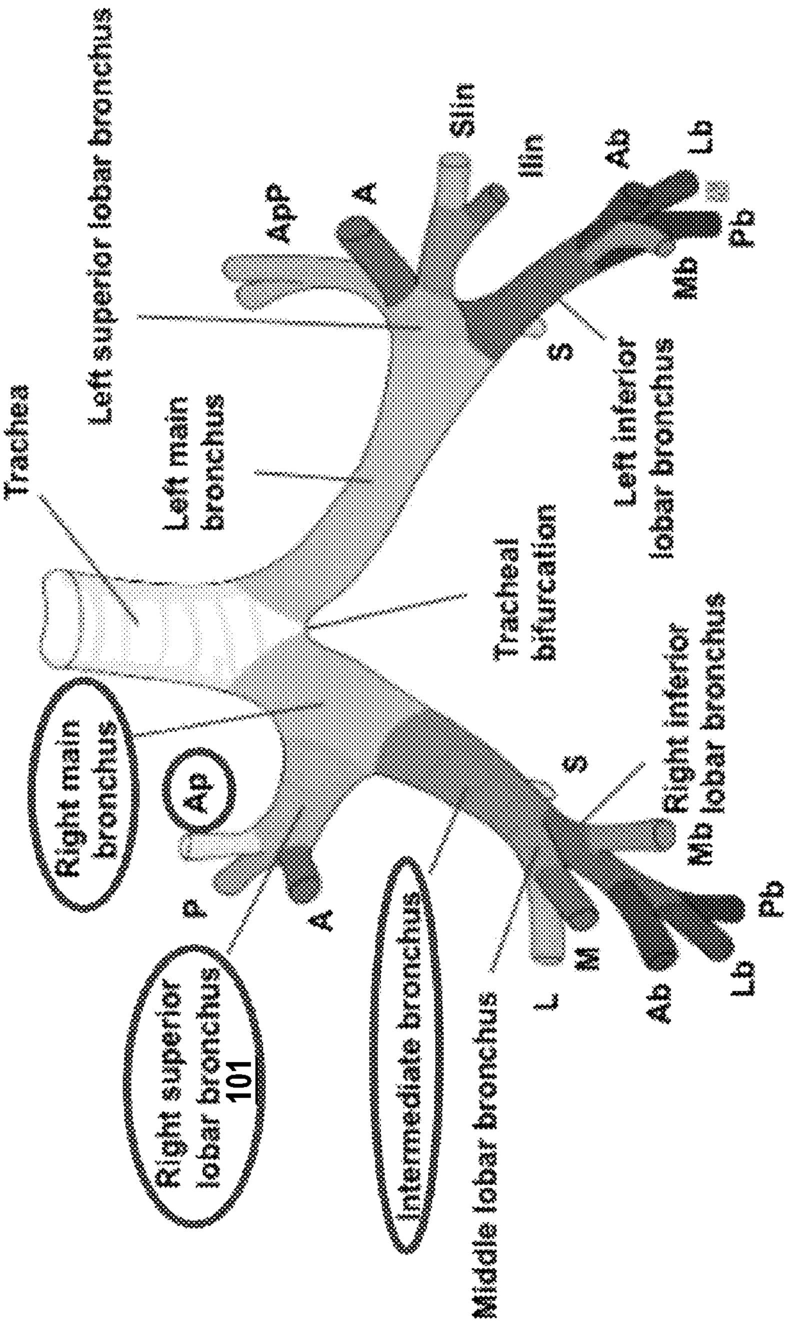
FIG. 1 schematically shows an example of a luminal network of a patient.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a device or system for bronchoscopy, one of skill in the art will appreciate that this is not intended to be limiting, and the devices described herein may be used for other therapeutic or diagnostic procedures and in various anatomical regions of a patient's body. The provided device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of. NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

Anti-Prolapse Passive Section

As described above, one challenge in bronchoscopy is reaching the upper lobe of the lung while navigating through the airways. FIG. 1 schematically shows an example of a luminal network 100 of a patient. In the illustrated embodiment, the luminal network 100 is a bronchial network of airways (i.e., lumens, branches) of the patient's lung.

Access to the peripheries of the right upper lobe 101 of the lung through the Apical segment (Ap) has been a challenge with conventional bronchoscopes. In the example 200 shown in FIG. 2, the sharp 180-degree angle between trachea and Ap combined with the large space at the junction of intermediate bronchus, right main bronchus, and the right upper lobar bronchus may cause bronchoscopes to kink and/or prolapse 201 downward through the intermediate bronchus. As sections of elongate device are curved as they are moved through the one or more passageways, the curved sections are subject to compression. The compression causes the elongate device to bend and contact the walls of one or more passageways along its length. In areas where there are one or more large passageways around the elongate device, when the distal end of the device encounters tissue resistance, the elongate device may bend within the large airway and move towards an unintended region of anatomy and not in the intended direction known as prolapsing. Prolapsing is more probable when tissue resistance gets higher (e.g., due to airways being too small, lung not fully inflated, diseased tissue, blind insertion, etc.).

Although the illustrated luminal network is a bronchial network of airways within the patient's lung, this disclosure is not limited to only the illustrated example. Prolapsing or kinking can happen when a flexible elongate member passes through any region in a subject body. The prolapse or kink may result in potential damage as it may expose the sharp edges of the kinked elongate device and complicate the surgical procedure. Moreover, a bent or kinked elongate device may render the system losing location/shape control of the device and it may block the passage of an instrument. Furthermore, a device that prolapses or kinks may not be able to provide adequate reach towards the target anatomy for performing the intended task. Current methods to solve the kink/prolapse issue may include detecting a prolapse, using shape sensing or force sensing to predict when prolapse may occur or using an outer sheath to provide kink resistance (a steerable outer sheath with sufficient stiffness to not kink and an endoscope or working channel placed is placed inside the outer sheath and extended over the outer sheath to reach a region). However, such methods require additional components, complicate the device or compromise the capability of reaching hard-to-reach body cavities and conduits.

The present disclose provides methods and systems to effectively prevent prolapse or kink without requiring extra sensors or additional elements. The anti-prolapse shaft design, systems and methods described herein may be used to navigate any type of luminal network, such as bronchial networks, renal networks, cardiovascular networks (e.g., arteries and veins), gastrointestinal tracts, urinary tracts, as described elsewhere herein.

Figure 2:
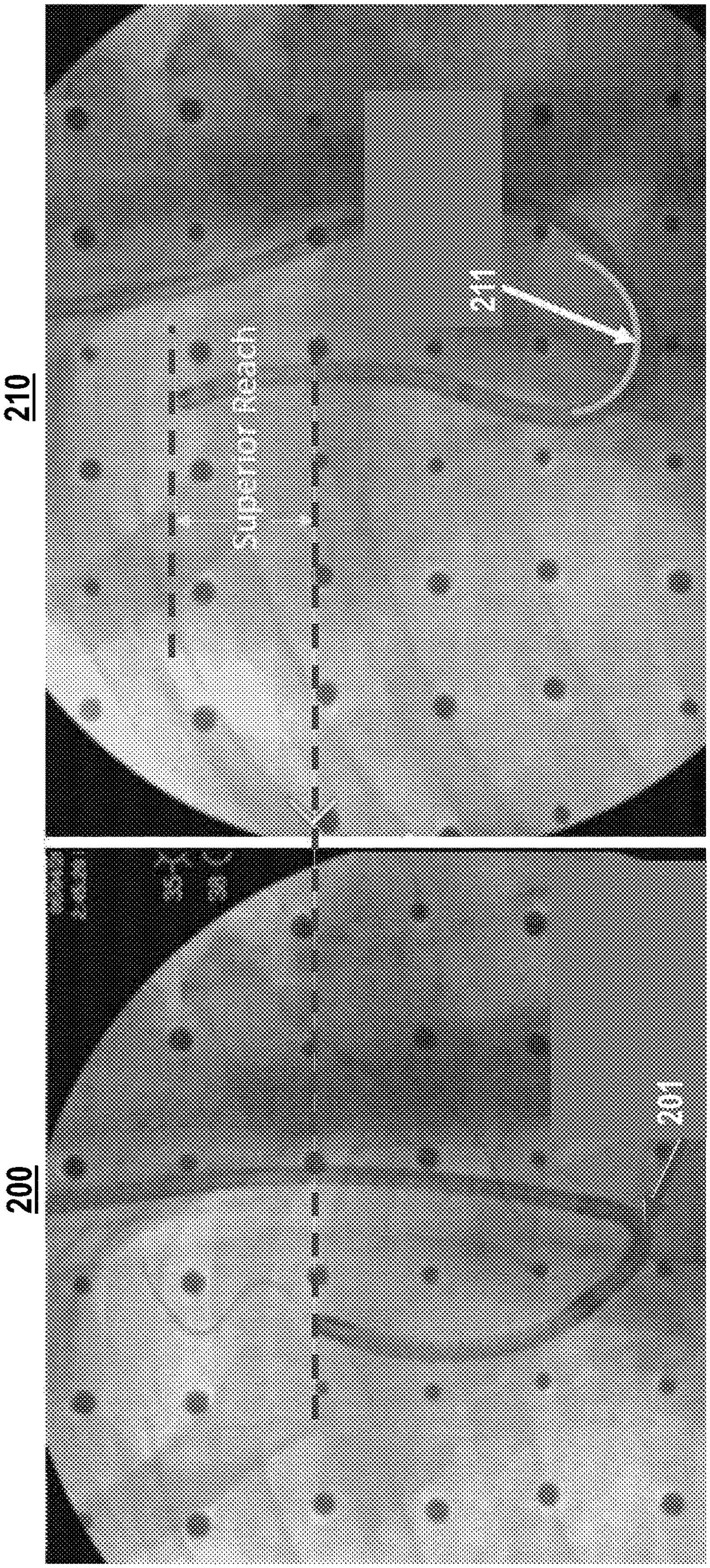
FIG. 2 shows an example of a flexible elongate member navigated through an airway/channel with improved anti-prolapse capability.

In an aspect of the present disclosure, a flexible endoscope with improved performance at reduced cost is provided. A flexible elongate member of the endoscope herein may have anti-prolapse capability that allows the elongate member to reach hard-to-reach body cavities and conduits. FIG. 2 shows an example 210 of the flexible elongate member navigated through an airway/channel with improved anti-prolapse capability. As illustrated in the example 210, the improved anti-prolapse capability may allow the elongate member to achieve superior reach compared to the example without such anti-prolapse feature. The capability of the elongate member to reach hard-to-reach body cavities and conduits may be constrained by a minimum bending radius 211 without kink or prolapse.

In some embodiments, the flexible elongate member may comprise multiple sections including an active steerable/bending section, a passive section, and a proximal shaft. The passive section may be formed with unique structures providing a minimum bend radius to prevent prolapse/kink. Such passive section may beneficially provide prolapse resistance and allow for improved capability of reaching the peripheries of the lung 210 compared to the conventional bronchoscopes as shown in the example 200. As shown in the example 210, as the bronchoscope is pushed through the tortuous path, the passive section may beneficially form a “bridge” configuration 211 over the large space within the right main bronchus which resists a prolapse into the intermediate bronchus. In contrast, the conventional device in the example 200 without such anti-prolapse passive section may kink or prolapse 201 when it moves through the same passageway.

Figure 3:
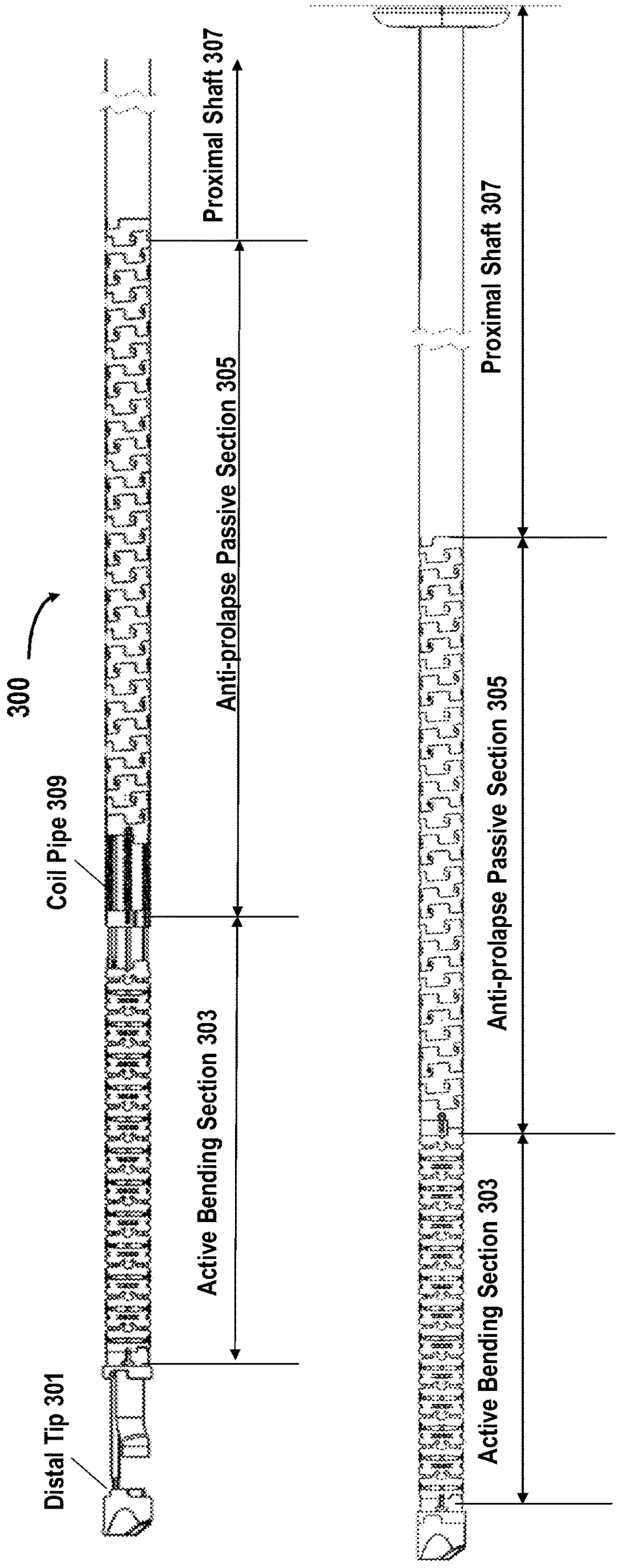
FIG. 3 shows an example of an elongate member of an endoscope with an anti-prolapse feature.

FIG. 3 shows an example of an elongate member 300 of an endoscope with an anti-prolapse feature. In some embodiments, a flexible elongate member may comprise multiple sections including an active steerable/bending section 303, a passive section 305, and a proximal shaft 307. The flexible elongate member may comprise a steerable tip 301 located at the distal end of the active bending section. Details about the distal tip are described later herein. The elongate member may comprise any other components such as coil pipes 309 anchored at a distal end of the passive section and a proximal end of the proximal shaft 307 to prevent unintended motion of the shaft during articulation of the bending section. The coil pipes may beneficially prevent muscling phenomenon. In some cases, tensioning the tendons in order to articulate the distal end may result in unwanted bending and torquing along the entire length of the flexible instrument, referred to as “muscling” and “curve alignment.” Details about the coil pipes are described later herein.

As shown in FIG. 3, the plurality of sections may be arranged along the length of the elongate member from the distal end to the proximal end. The anti-prolapse passive section 305 may be connected to the active bending section at a first end and connected to the proximal shaft 307 at a second end. Although three sections are illustrated in the example, in some embodiments, the elongate member may include more or fewer sections. For example, the elongate member can include one, two, three, four, five, six, seven, or more sections. The elongate member may also include any number of anti-prolapse passive sections. For example, there may be two or more passive sections with the anti-prolapse mechanism.

The passive section may comprise a mechanism for limiting a minimum bend radius of the passive section thereby preventing prolapse. The minimum bend radius may be defined or determined by a structure of the passive section. In some embodiments, the minimum bend radius of the passive section may be greater than a minimum bend radius of the active bending section 303.

Figure 4:
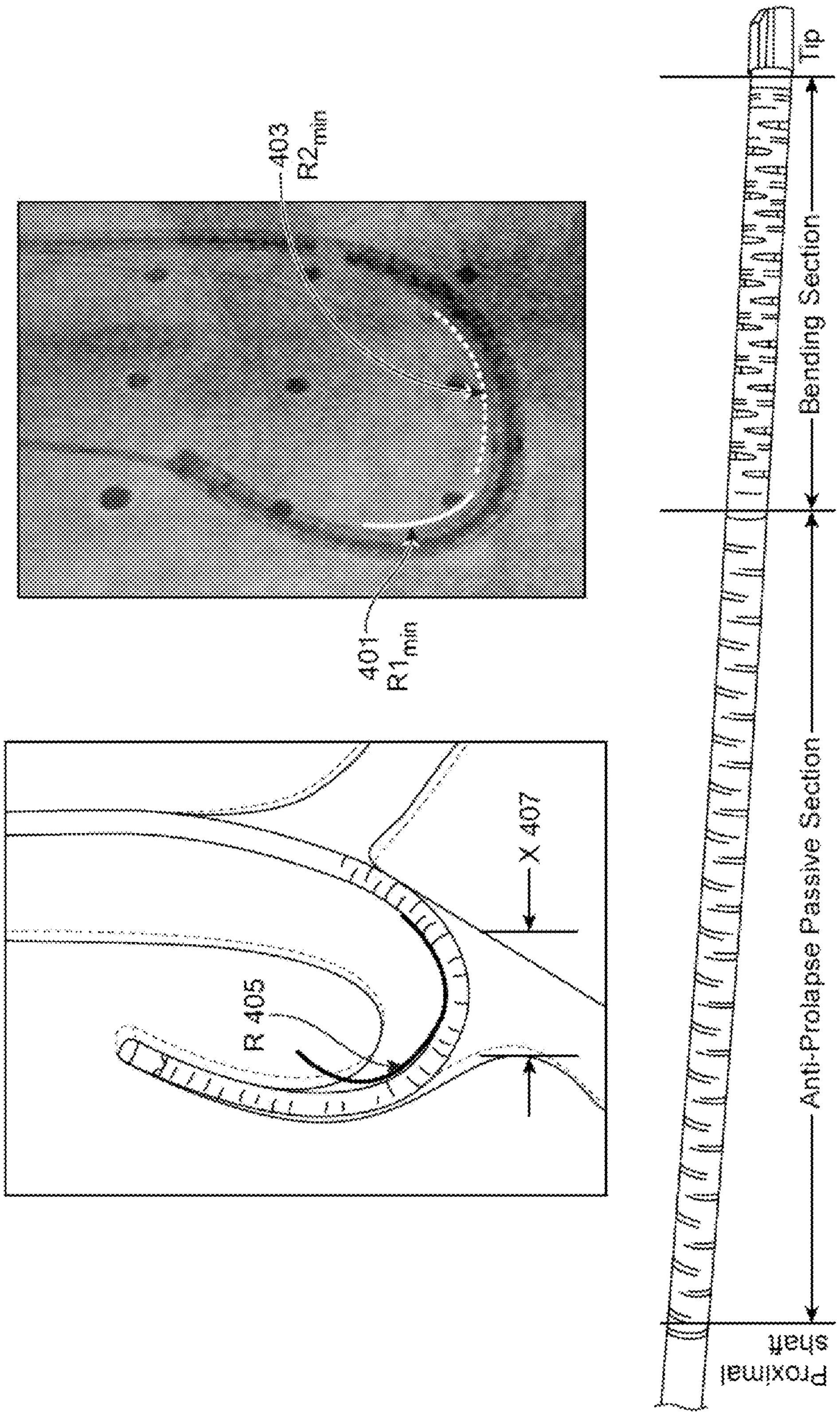
FIG. 4 shows an example of different minimum bend radii of an active bending section and a passive section.

FIG. 4 shows an example of the different minimum bend radii of the active bending section and the passive section. As shown in the example, the minimum bend radius 401 ($\mathbf{R1}_{min}$) of the active bending section may be smaller than the minimum bend radius ($\mathbf{R2}_{min}$) 403 of the passive section. The different minimum bend radii of the active bending section and passive section beneficially facilitates maneuverability of the elongated member, while preventing or reducing the likelihood of kinking or prolapsing. Alternatively, depending on the tortuosity, curvature or size of the passageway or other requirement, the minimum bend radius of the active bending section may be substantially the same or greater than the minimum bend radius of the anti-prolapse passive section.

The smaller minimum bend radius ($\mathbf{R1}_{min}$) 401 in the active bending section or the section closer to the tip may facilitate alignment of the tip with the airways in a tight space or with sharp turns. For example, the minimum bend radius ($\mathbf{R1}_{min}$) of the active bending section may be in a range of 5 mm-30 mm, a range of 8 mm-15 mm or any number below 5 mm or above 30 mm. This minimum bend radius may allow the active bending section to achieve articulation of at least 120-degree, 130-degree, 140-degree, 150-degree, 160-degree, 170-degree, 180-degree, 190-degree, 200-degree or greater.

In some cases, the relatively larger minimum bend radius ($\mathbf{R2}_{min}$) 403 of the passive section may help to bridge the gap in the right main bronchus and/or prevent prolapsing. The minimum bend radius ($\mathbf{R2}_{min}$) 403 of the passive section may be in a range of 1 cm-3 cm or any number below 1 cm or greater than 3 cm. In some cases, the minimum bend radius of the passive section may be determined based on a curvature or size of the passageway inside a patient. For instance, the minimum bend radius of the passive section (i.e., radius of the curvature) (e.g., R 405) may be greater than or substantially equal to the size of the gap X 407 in the right main bronchus.

In some embodiments, the mechanism for limiting the minimum bend radius in the passive section may comprise integrally formed mechanical features (e.g., cut pattern) which prevent the passive section to bend any further beyond a minimum bend radius. Details about the mechanical features or structures are described with respect to FIG. 5 and FIG. 6. By varying a dimension, shape or other design of the structures, the device herein allows for improved flexibility for configuring the minimum bending radius at selected section or location along the elongate member. For example, by selecting a dimension, shape or size of the mechanical feature formed at a selected location in the passive section, a minimum bend radius 405 of the passive section (i.e., radius of the curvature) may be greater than or substantially equal to the size of the gap X 407 in the right main bronchus.

Referring back to FIG. 3, the minimum bending radius of the active bending section 303 and the anti-prolapse passive section 305 may be different. In some cases, the different minimum bend radii may be defined by varying the mechanical structures (e.g., a cut pattern) of the active bending section and/or the passive section. In some cases, the active bending section and the passive section may be formed of the same material (e.g., stainless steel) whereas the minimum bend radius may be different by varying a cut pattern. For example, by selecting a gap size (width of the gap) and/or pitch of repeated cut pattern, different minimum bend radius may be achieved. For instance, greater gap size such as greater width of the gap may correspond to smaller bend radius, and smaller pitch of the repeated cut pattern (i.e., repeated gaps) may correspond to smaller bend radius.

The material of the active bending section or the passive section may or may not be the same. For example, the material of the active bending section and/or the passive section may include metallic materials such as stainless steel or nitinol, stiff polymers such as PEEK, glass or carbon filled PEEK, Ultem, Polysulfone and other suitable materials. In some cases, the material allowing for easier manufacturing (e.g., laser cut pattern) may be selected thereby reducing the fabrication cost.

The stiffness of the active bending section and the passive section may or may not be the same. In some cases, the stiffness of the active bending section or the passive section may be substantially the same whereas the minimum bend radius is different. For instance, when the bending has not reached the minimum bend radius, the stiffness of the active and passive sections may be substantially the same. Alternatively, the stiffness of the active bending section, the passive section and the proximal shaft section may be different. For instance, the more proximally located sections (e.g., proximal shaft 307) may be stiffer to provide pushability for the elongate member 300. In some cases, each section may be configured to provide a different flexibility or bending stiffness to facilitate a medical procedure and/or improve the drivability and control of the elongate member 300. For example, the active bending section 303 may provide steerability to the distal end of the bronchoscope with the smallest minimum bend radius. The passive section 305 may provide sufficient flexibility to advantageously follow the active bending section into the peripheral or upper lobes of the lung, for example, in the case of the bronchoscopy. The passive section 305 may further comprise the anti-prolapse mechanism as described above to prevent kinking. The proximal shaft section 307 may be flexible enough to be inserted through an introducer and inside a patient body, but pushable/rigid enough to provide support for the elongated member while an external portion of proximal shaft may remain external to a patient during a procedure (e.g., does not enter the introducer) and is stiff enough to provide support for the entire elongate member 300.

The lengths of the multiple sections may be selected depending on the use application or requirement. For example, the active bending section may be between about 40 and 90 mm, or approximately 50 mm in length; the passive section may be between about 50 mm and 150 mm, or approximately 80 mm; the proximal shaft section may be between about 500 mm and 1000 mm, or approximately 770 mm. The length of the different sections may vary depending on the type of the medical application/device or other factors.

As described above, in some embodiments of the passive section, the minimum bend radius of the passive section may be defined or determined by an integrally formed structure of the passive section. In some embodiments, the structure may be a cut pattern formed on a substantially tubular component. In some cases, the cut pattern may comprise features/structures such that by varying a gap size and/or pitch of the features different minimum bend radii may be achieved.

Figure 5:
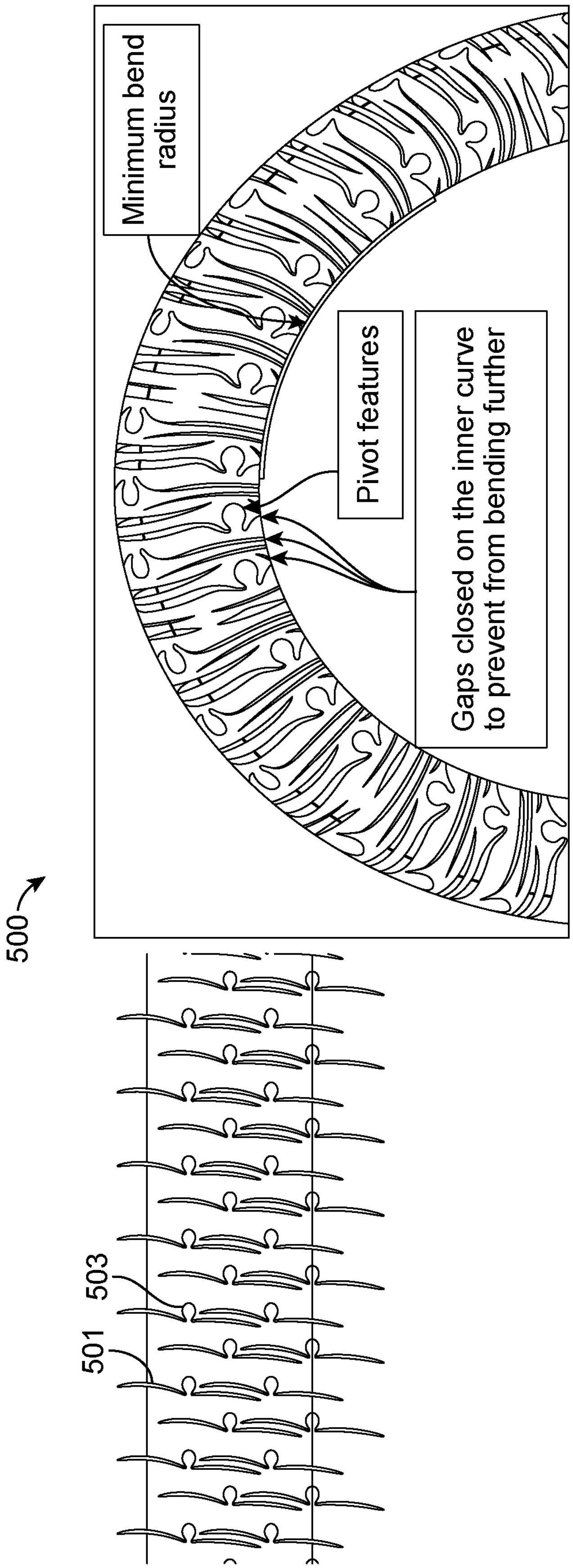
FIG. 5 and FIG. 6 show different examples of features for the anti-prolapse passive section.
Figure 6:
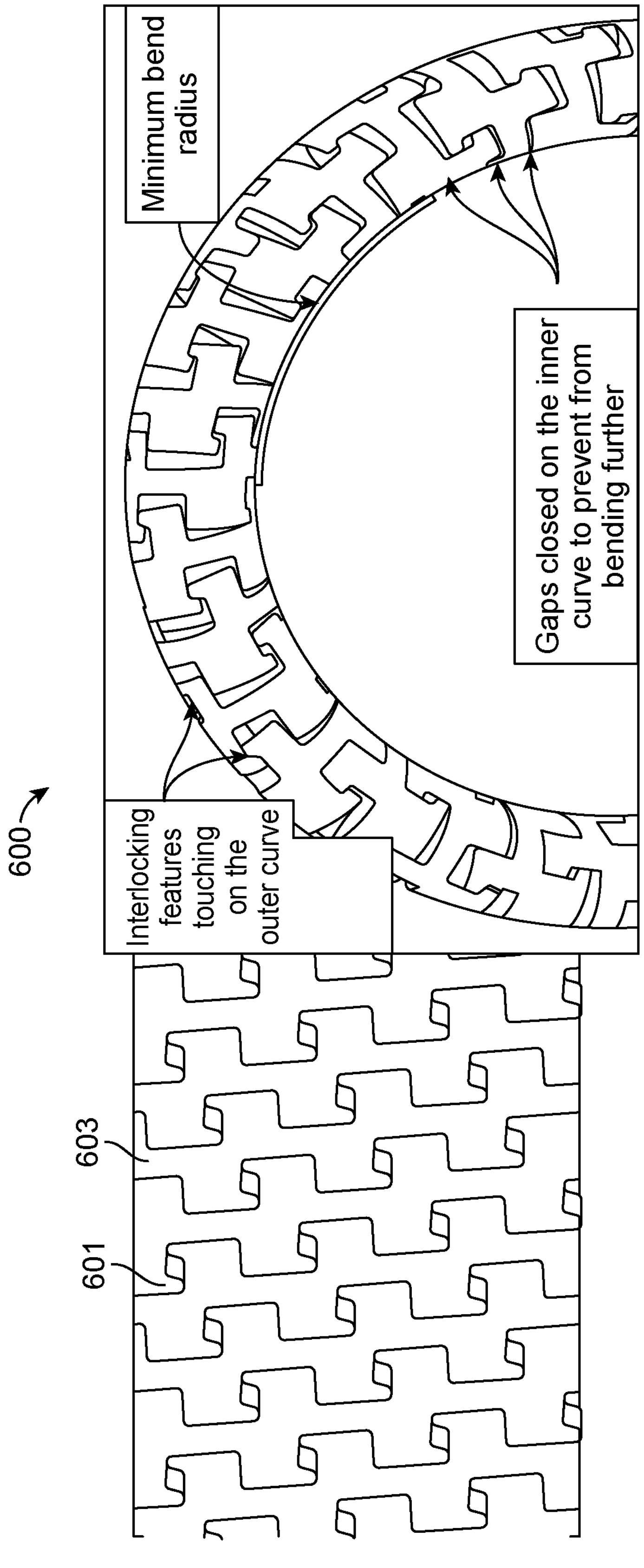

FIG. 5 and FIG. 6 show different examples of the features for the anti-prolapse passive section. FIG. 5 shows an example 500 of "ball and socket" cut pattern. The cut pattern may comprise a plurality of repeated gaps 501 and pivot features 503. As illustrated in the example, the minimum bend radius may be reached when the gaps 501 are closed on the inner curve thereby preventing the passive section from bending any further. In some cases, a bend radius at which all the gaps on the inner curve are closed may be defined as the minimum bend radius. The pivot features 503 may also help to prevent prolapse or kink by the interlocking configuration formed on the outer curve. In some cases, when the minimum bending radius is smaller than certain threshold (e.g., in order to achieve better flexibility or degree of bending), kink or prolapse may occur. The gap size and/or pitch of the repeated pattern may be selected to achieve a minimum bending radius that is above the threshold. In some cases, the threshold for the minimum bending radius may be determined based on empirical data (e.g., experiments data) and/or simulation results.

FIG. 6 shows an example 600 of continuous spiral cut pattern with interlocking features 601. The cut pattern may comprise a plurality of gaps 603 and interlocking features 601. As illustrated in the example, the minimum bend radius may be reached when the gaps are closed on the inner curve thereby preventing the passive section from bending any further while the interlocking features on the outer curve come into contact or form a locking configuration. It should be noted that the examples of the cut pattern are for illustration purpose only, any other cut pattern may be used. As described above, the gaps, interlocking features or the pivot features can be formed using any suitable manufacturing method including but not limited to, laser cut, molding, machining, and the like.

The cut pattern for the active bending section, passive section and the proximal bending section may be different. In some cases, the cut pattern for the passive section may allow for isotropic bending and the features such as the gaps and interlocking features may effectively prevent kinking as described above. In some cases, a different cut pattern (e.g., braid structures) may be employed for the proximal shaft for providing high axial and torsional stiffness and greater control over the stiffness profile. The proximal shaft section may prevent kinking or prolapse due to the greater stiffness of the section. Such integrally formed features (cut pattern) beneficially prevent kinking or prolapse without requiring additional components.

Active Bending Section

Figure 7:
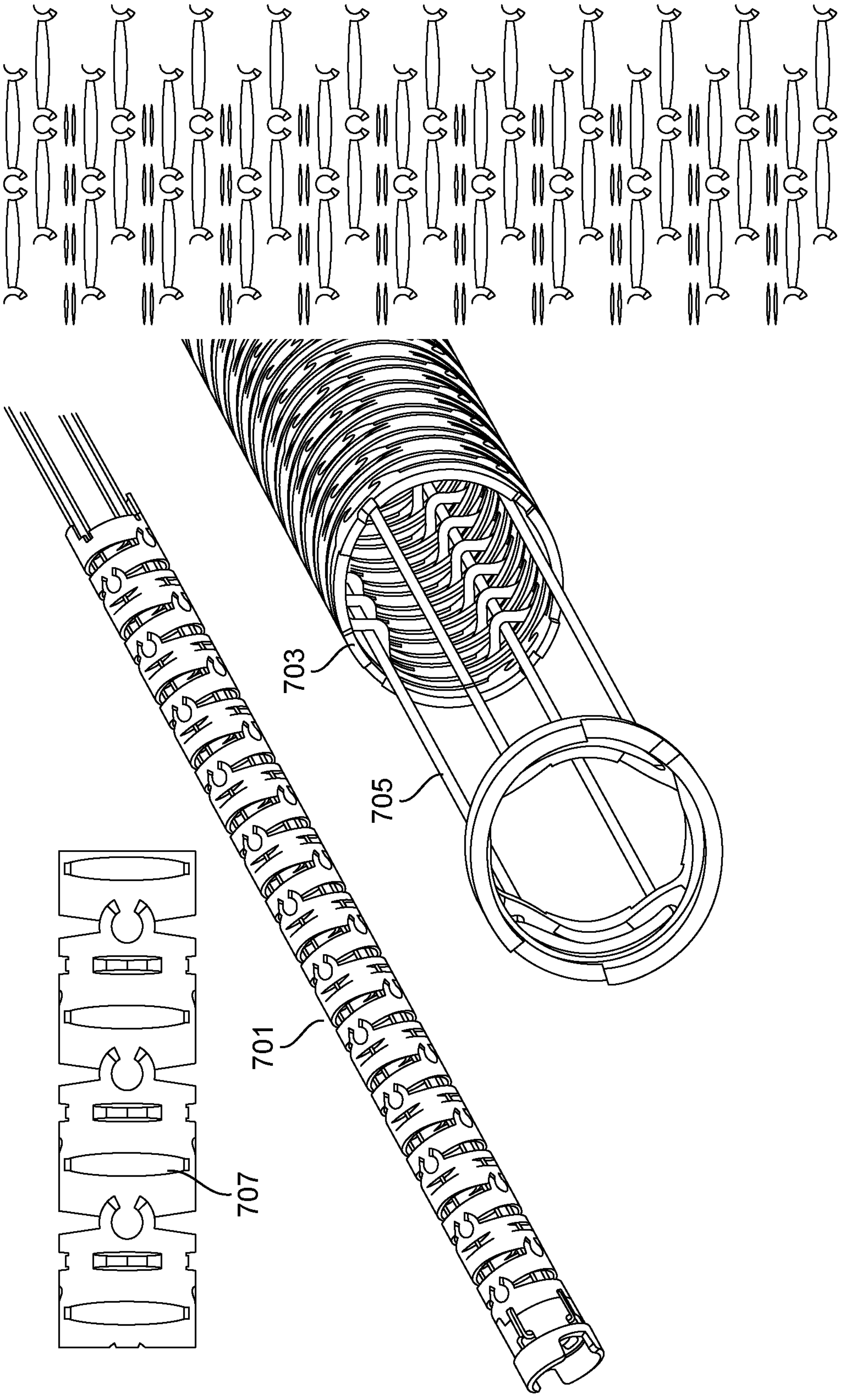
FIG. 7 shows an example of an active bending section.

FIG. 7 shows an example of an active bending section 701. In some embodiments, the active bending section may comprise inner structures such as eyelet structures 703 to pass through a plurality of pull wires 705. As shown in the example, a pull wire 705 may run through a series of eyelet structures along the length of the bending section. The eyelet structures may be integrally formed with the active bending section on an inner surface of the active bending section to hold the pull wire in place while allowing for a relative axial movement of the pull wire.

As shown in the example, a cut pattern of the active bending section may be different from the cut pattern of the passive section. For example, the gaps 707 in the active bending section may be greater than those of the passive section thereby allowing for a smaller minimum bend radius. Additionally or alternatively, a pitch of the pattern in the active bending section may be smaller than the pitch in the passive section. In some cases, the internal eyelet structure may be formed with the same pitch of the cut pattern. A smaller pitch of the eyelet structures may beneficially prevent kinking of the pull wire when the pull wire is placed inside of the series of eyelet structures.

Figure 8:
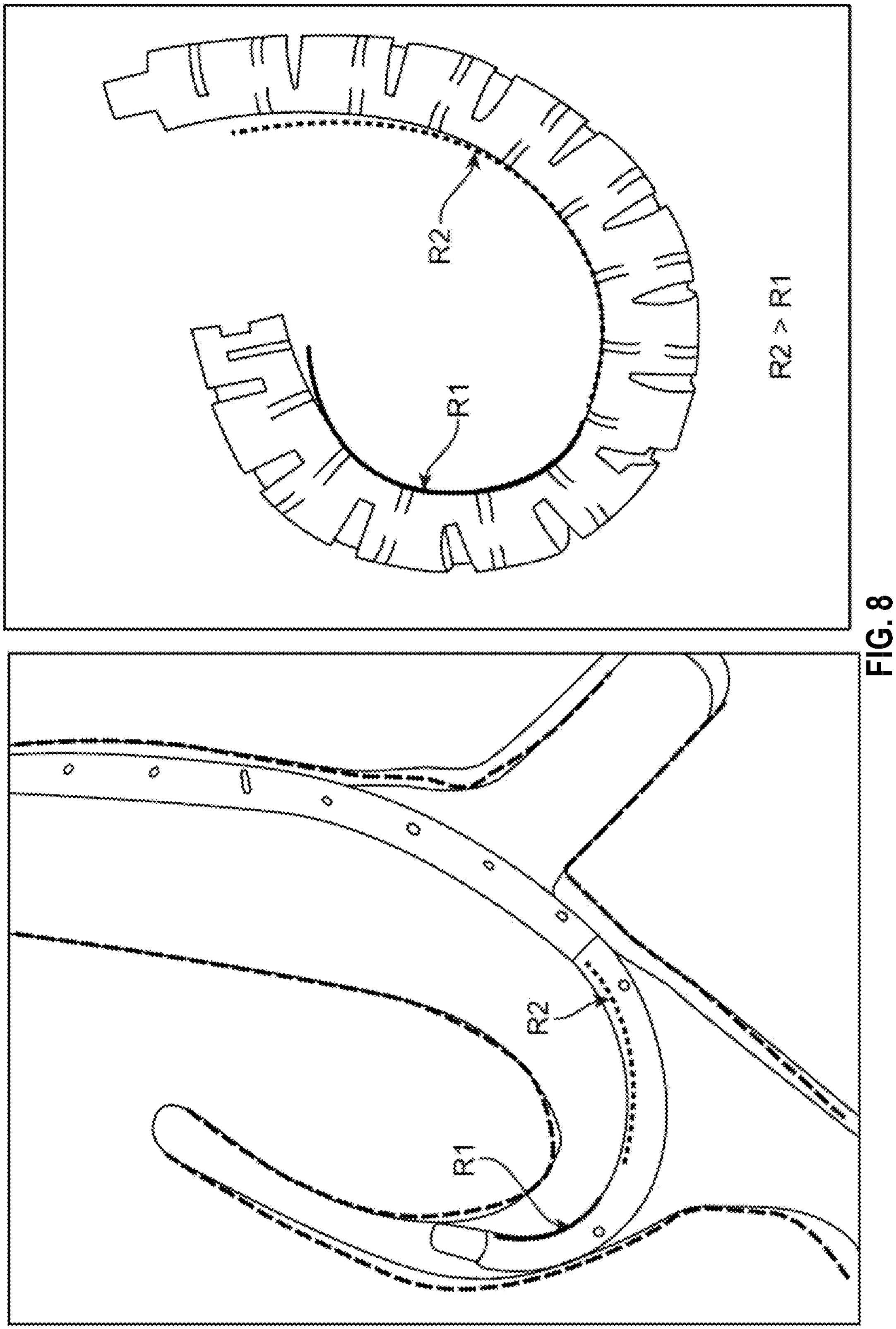
FIG. 8 shows an example of an active bending section with two discrete minimum bend radii.

In some embodiments, in addition to or instead of having constant minimum bending radius within the active bending section or the passive section, variable minimum bending radius may be provided. For example, the active bending section may have two or more bend radii. As an example, a minimum bend radius in the active bending section may increase from the distal end to the proximal end. The change of the minimum bend radius may be gradual or discrete. FIG. 8 shows an example of an active bending section with two discrete minimum bend radii $R_1$, $R_2$ ($R_2>R_1$). The varied minimum bend radius may be achieved by varying the cut pattern. For example, the minimum bend radius may be increased by decreasing a gap size or increasing the pitch of the cut pattern.

FIG. 9 shows an example of a bending section with a uniform minimum bend radius R1. In some cases, when the minimum bending radius is smaller than certain threshold (e.g., in order to achieve better flexibility or degree of bending), kink or prolapse may occur. As shown in the example 901, when the minimum bend radius is below a threshold, stress concentration increases in the area and makes it easier to kink and prolapse. In some embodiments, the overall length and minimum bend radii may vary long the length of the elongate member. In some cases, a laser-cut construction (e.g., same "dog-bone" shape) may be applied to the entire section whereas a size/dimension of the pattern (e.g., pitch, gap size) may vary to change the minimum bend radius. Alternatively or additionally, the pattern may also change along the length of the elongate member.

Figure 3A:
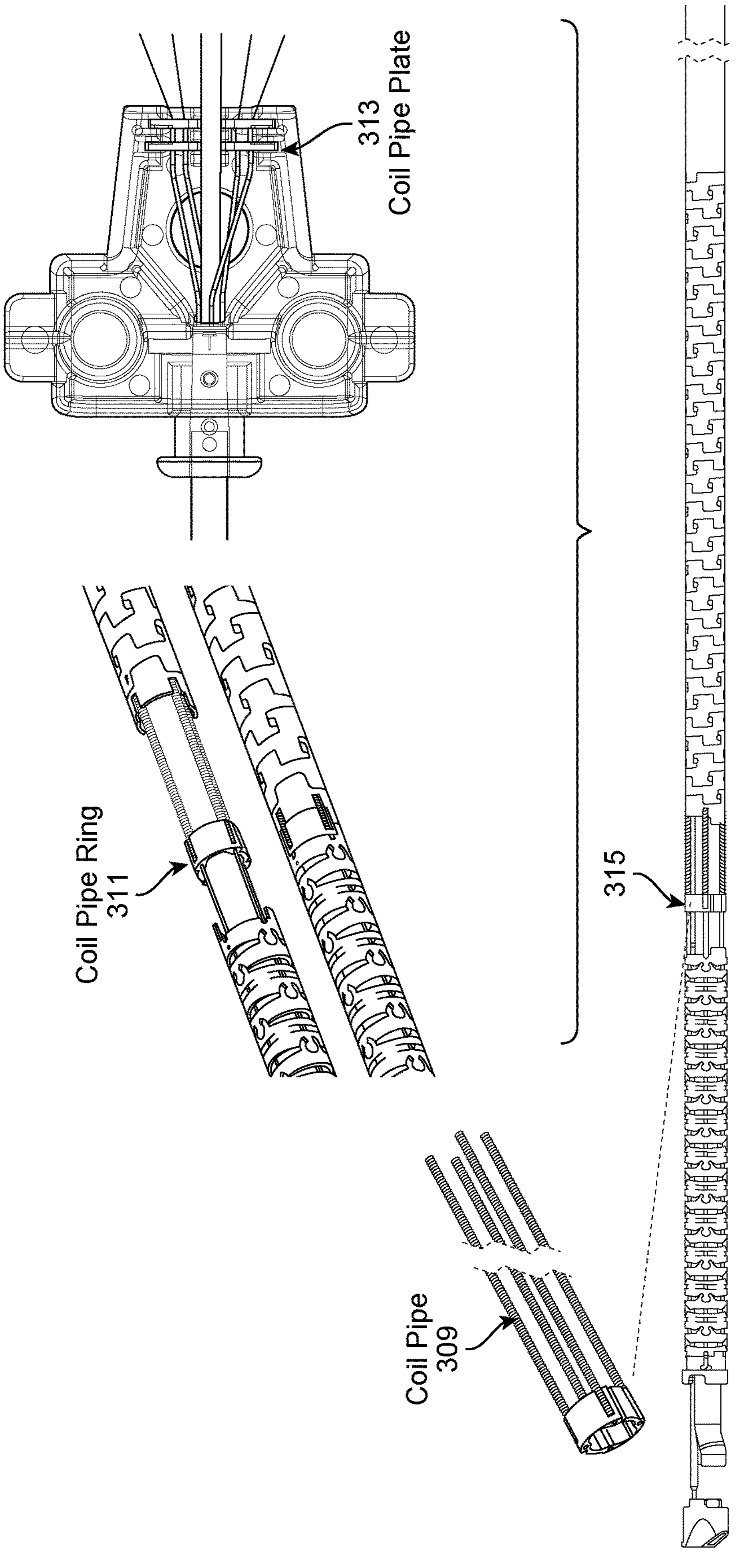
FIG. 3A shows an example of integrating coil pipes into the medical instrument.

As described above, in some embodiments, the elongate member may comprise any other components such as coil pipes anchored at a distal end of the passive section and a proximal end of the proximal shaft to prevent unintended motion of the shaft during articulation of the bending section. The coil pipes may beneficially prevent muscling phenomenon. FIG. 3A shows an example of integrating coil pipes into the medical instrument. In some cases, at least one, two, three, four, five or more coil pipes may be included to reduce the axial compression/extension (strain) of the elongate member during articulation of the bending section. The coil pipes may transmit at least a portion of the articulation load applied to the active bending section and/or the shaft back to the handle (e.g., via actuator or motors that drive one or more articulating pull wires)

The coil pipes may counteract the articulation loads allowing for an improved stability of the proximal shaft and the anti-prolapse passive section. The plurality of coil pipes 309 may reside within the lumen of the shaft tube and the passive section (i.e., tube bore), and be configured to transfer articulation reaction forces from the bending section to the handle portion. The load transmission tubes are configured to transfer the bending section articulation reaction forces back to the handle portion thereby reducing the articulation forces that would have been applied to the proximal shaft and the anti-prolapse passive section. Such design may beneficially prevent these articulation forces from being resolved through the proximal shaft and the anti-prolapse passive section thus providing a stable elongate member. The transmission modality described herein may ensure that the proximal shaft and the anti-prolapse passive section experiences minimal axial compressive or extension forces, thereby remaining stable during the articulation of the bending section.

In preferred embodiments of the coil pipe mechanism, the plurality coil pipes may be longer than the length of the proximal shaft and the anti-prolapse passive section. The length of the coil pipes may be determined such that when they are under axial compression, the coil pies are still longer than the length of the proximal shaft and the anti-prolapse passive section thereby preventing loads from transferring through the proximal shaft and the anti-prolapse passive section. For example, the length of the load transmission tubes may be at least 0.01%, 0.1%, 0.2%, 0.3%, 1%, 5%, 10% longer than the total length of the proximal shaft and the anti-prolapse passive section.

A distal end of the coil pipes may be anchored to an interface 315 between the anti-prolapse passive section and the active bending section. For example, the distal end of the coil pipes may be mechanically constrained within a counterbore feature or soldered, welded or glued to a coil pipe ring structure 311. The coil pipe ring may beneficially prevent the distal end movement of the coil pipes. A proximal end of the coil pipes may be anchored to a coil pipe plate 313 located at the handle (or proximal portion of the endoscope) thereby preventing movement of the proximal end of the coil pipes. The coil pipes may be compressed between the two anchor points and may have a longer path from the proximal end to the distal end of the scope relative to path through the neutral axis of the scope. The anchoring of coil pipes at both ends combined with the excess length of the coil pipes allows the pull wires to travel through a constant distance between the two anchoring points regardless of the shape of the scope through tortuous anatomy which prevents the unintended motion of the shaft during articulation of the bending section.

The coil pipes may have any configuration between the two anchoring points so long as the configuration that can accommodate a displacement within the shaft tube. For example, when the passive section or proximal shaft is bent such as due to being subjected to a tortuous anatomy, the shaft tube or the passive section may cause displacement of components housed within the bore of the shaft tube and the passive section. In this case, the extra length of the coil pipes may beneficially accommodate the displacement within the shaft tube bore or the passive section while improving stability of the elongate member.

Figure 3B:
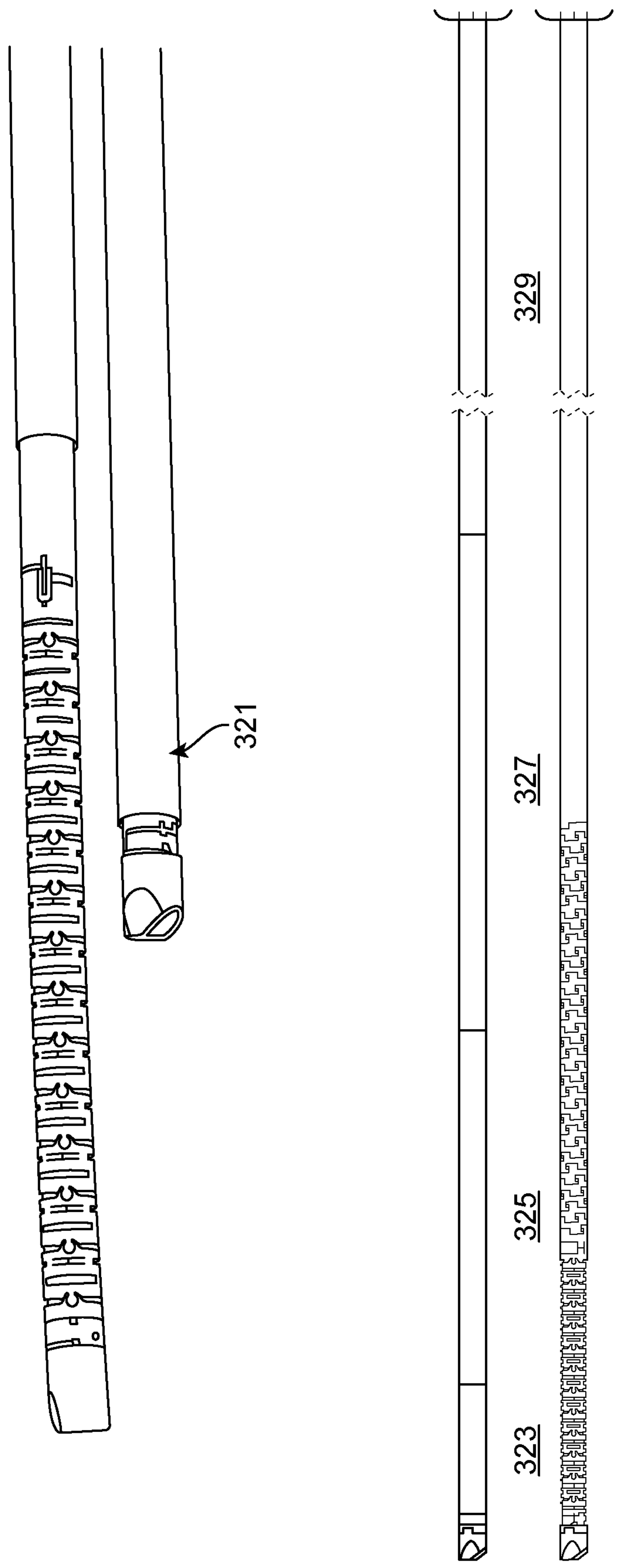
FIG. 3B shows an example of a jacket applied over the catheter.

In some embodiments, the elongate member may comprise a sleeve or jacket. FIG. 3B shows an example of a jacket 321 applied over the catheter. The jacket 321 may slip over the active bending section, anti-prolapse passive section, and proximal shaft of scope. The jacket may be formed of polymer or any suitable material such as PTFE, pebax, polyurethane, or nylon. In some cases, the jacket may be manufactured by polymer extrusion. The jacket may have multiple layers including braiding to provide torsional stiffness to the elongate member. In some embodiments, the jacket may have a variable stiffness profile along the length. For example, the jacket may have a two, three, four or more different stiffness or multiple segments 323, 325, 327, 329 with different stiffness along the length of the catheter by having extrusions of different durometers laminated together. In some cases, the stiffness of a segment closer to the distal end of the catheter (e.g., segment 323) may be smaller than the stiffness of a segment closer to the proximal end (e.g., segment 239). The different segments 323, 325, 327, 329 may or may not correspond to the active bending section, passive section and proximal shaft.

Figure 3C:
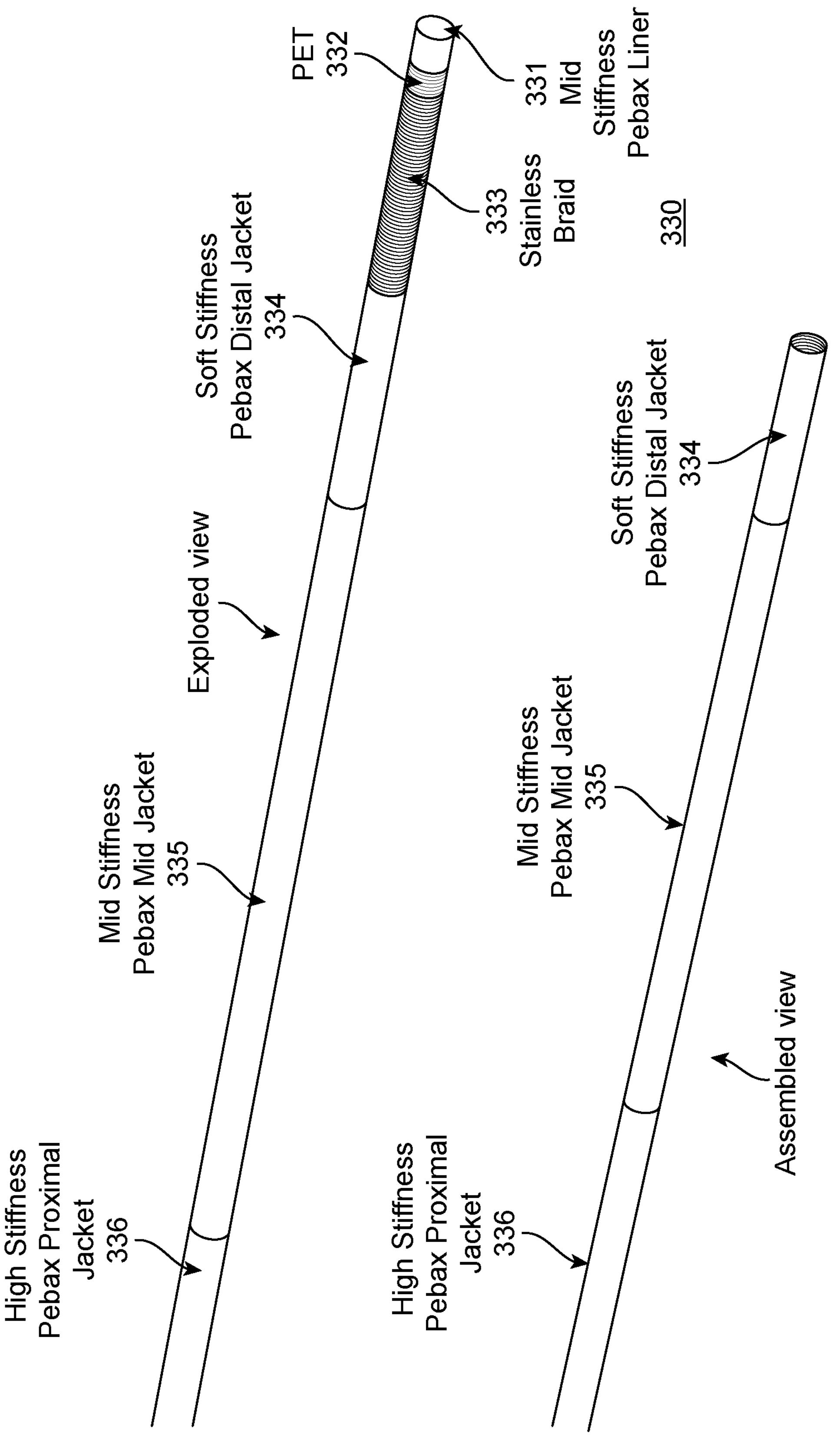
FIG. 3C shows an example of a jacket comprising multiple sections.

FIG. 3C shows another example 330 of a jacket comprising a plurality of segments and/or layers having different stiffness. In some embodiments, the dimension, materials and/or features forming the various segments of the jacket may be selected to provide a smooth outer layer and/or variable stiffness. This beneficially provides sufficient support or stiffness in the proximal portion of the endoscope while maintaining flexibility in the distal portion of the endoscope. In the illustrated exploded view of the exemplary jacket, the jacket may comprise an inner layer 331 having a mid-level of stiffness. The inner layer 331 may be formed of pebax liner that is extend throughout the endoscope shaft. The jacket 330 may comprise a second layer 333 coming outside of the inner layer. In the illustrated example, the second layer may be formed of Stainless Steel braid. In some cases, stainless steel braid may be selected with optimal pitch and pattern to provide a desirable stiffness. The stainless steel braid may have pitch per inch (PPI) in an optimal range to provide desirable stiffness. For instance, a stainless steel braid with 70 pitch per inch (PPI)+/−30 PPI (Full Pattern) may be utilized. The jacket 330 may further comprise a third component 332 formed of polyethylene terephthalate (PET) to encapsulate the stainless steel braid 333 at the distal end. The third component 332 may come outside of the stainless steel braid 333 and substantially locate at the distal end. The jacket 300 may comprise an outer layer. The outer layer may comprise a plurality of segments 334, 335, 336. In some cases, the outer layer of the jacket may comprise a distal segment 334 formed of soft stiffness Pebax, a mid segment 335 formed of mid stiffness Pebax and a proximal segment 336 formed of high stiffness Pebax. The Pebax material forming the out layer of the jacket may contain low friction additives such as ProPell, Mobilize or similar to decrease the friction on the external surface of the jacket. It should be noted that the materials and dimension of the various segments are for illustration purpose only and one of skill in the art will appreciate that this is not intended to be limiting.

Flexible Endoscope

Figure 10:
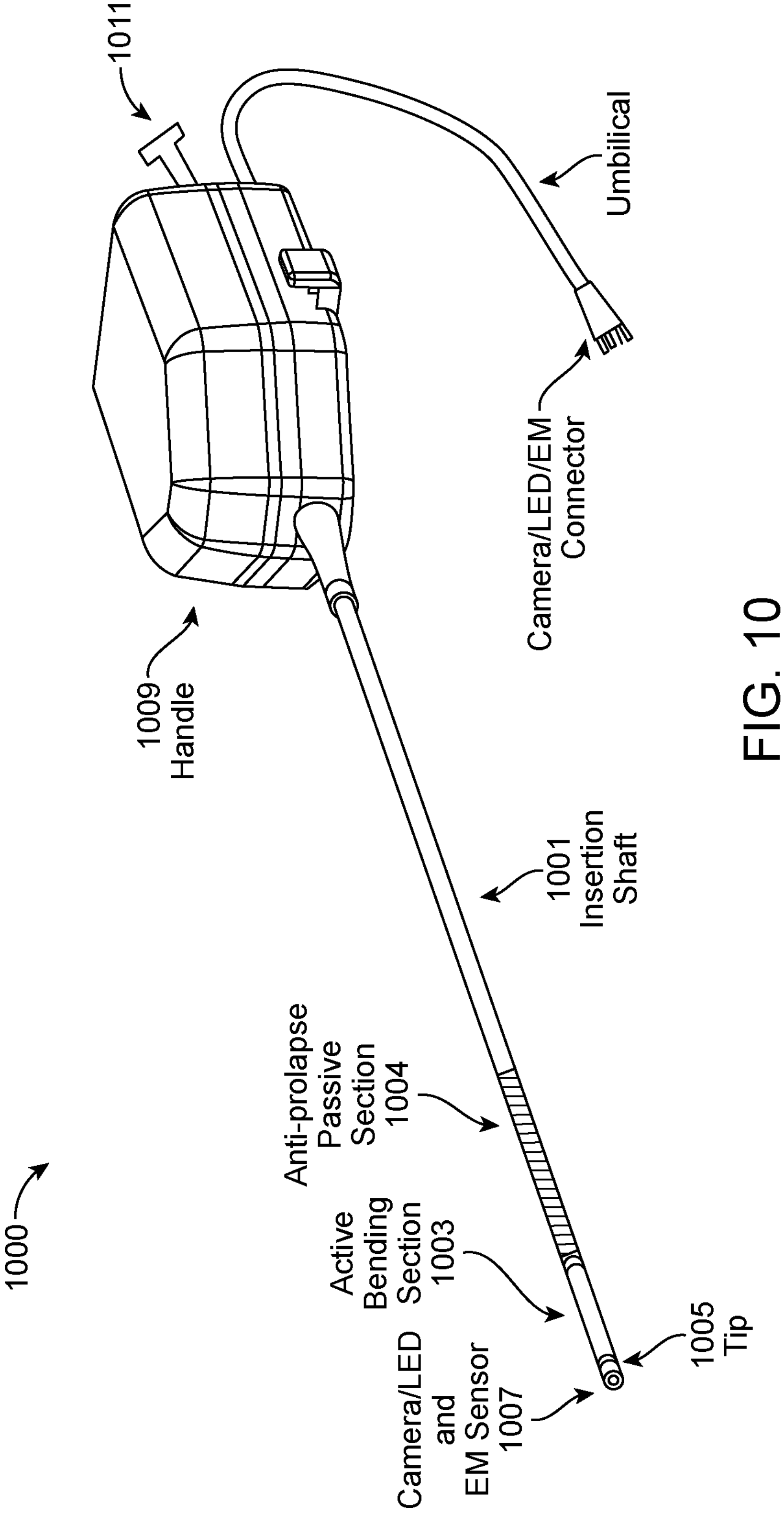
FIG. 10 illustrates an example of a flexible endoscope, in accordance with some embodiments of the present disclosure.

In some embodiments, the anti-prolapse mechanism herein may be utilized for improving reliability and stability of a flexible endoscope. The provided anti-prolapse mechanism may be utilized by any devices or apparatuses. In an aspect of the invention, a flexible endoscope with improved performance (e.g., improved reliability) at reduced cost is provided. FIG. 10 illustrates an example of a flexible endoscope 1000, in accordance with some embodiments of the present disclosure. As shown in FIG. 10, the flexible endoscope 1000 may comprise a handle/proximal portion 1009 and a flexible elongate member to be inserted inside of a subject. The flexible elongate member can be the same as the one described above. In some embodiments, the flexible elongate member may comprise a proximal shaft (e.g., insertion shaft 1001), steerable tip (e.g., tip 1005), a steerable section (active bending section 1003) and an anti-prolapse passive section 1004. The active bending section, an anti-prolapse passive section and the proximal shaft section can be the same as those described elsewhere herein. The endoscope 100 may also be referred to as steerable catheter assembly as described elsewhere herein. In some cases, the endoscope 100 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiment, the endoscope may contain varying levels of stiffness along the shaft, as to improve functional operation.

The endoscope or steerable catheter assembly 1000 may comprise a handle portion 1009 that may include one or more components configured to process image data, provide power, or establish communication with other external devices. For instance, the handle portion may include a circuitry and communication elements that enables electrical communication between the steerable catheter assembly 1000 and an instrument driving mechanism (not shown), and any other external system or devices. In another example, the handle portion 1009 may comprise circuitry elements such as power sources for powering the electronics (e.g., camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design the disposable endoscope. The handle portion or proximal portion may provide an electrical and mechanical interface to allow for electrical communication and mechanical communication with the instrument driving mechanism. The instrument driving mechanism may comprise a set of motors that are actuated to rotationally drive a set of pull wires of the catheter. The handle portion of the catheter assembly may be mounted onto the instrument drive mechanism so that its pulley/capstans assemblies are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

The electrical interface (e.g., printed circuit board) may allow image/video data and/or sensor data to be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 1009 may comprise one or more mechanical control modules such as lure 1011 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 1000. The mechanical interface may allow the steerable catheter assembly 1000 to be releasably coupled to the instrument driving mechanism. For instance, the handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool. Details about the instrument driving mechanism are described later herein.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 1007 is located at the tip of the catheter or endoscope shaft 1005. For example, line of sight of the camera may be controlled by controlling the articulation of the active bending section 1003. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optimal component.

The distal tip 1005 may be a rigid component that allow for positioning sensors such as electromagnetic (EM) sensors, imaging devices (e.g., camera) and other electronic components (e.g., LED light source) being embedded at the distal tip.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site.

The endoscope may have a unique design in the elongate member. In some cases, the active bending section 1003, the anti-prolapse passive section and the proximal shaft of the endoscope may consist of a single tube that incorporates a series of cuts (e.g., reliefs, slits, etc.) along its length to allow for improved flexibility, a desirable stiffness as well as the anti-prolapse feature (e.g., features to define a minimum bend radius).

As described above, the active bending section 1003 may be designed to allow for bending in two or more degrees of freedom (e.g., articulation). A greater bending degree such as 180 and 270 degrees (or other articulation parameters for clinical indications) can be achieved by the unique structure of the active bending section while kinking or prolapse may be prevented by the passive section following the active bending section. In some cases, the active bending section and/or the passive section may be fabricated separately as a modular component and assembled to the proximal shaft. In some cases, the cut patterns of the active bending and passive sections may be different such that at least the minimum bend radius of the two sections may be different. In some cases, a variable minimum bend radius along the axial axis of the elongate member may be provided such that an active bending section or the passive section may comprise two or more different minimum bend radii.

The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

In some embodiments, the proximal end or portion of one or more pull wires may be operatively coupled to various mechanisms (e.g., gears, pulleys, capstans, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The pull wires may be made of any suitable material such as stainless steel (e.g., SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The proximal design may improve the reliability of the device without introducing extra cost allowing for a low-cost single-use endoscope. In another aspect of the invention, a single-use robotic endoscope is provided. The robotic endoscope may be a bronchoscope and can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 11:
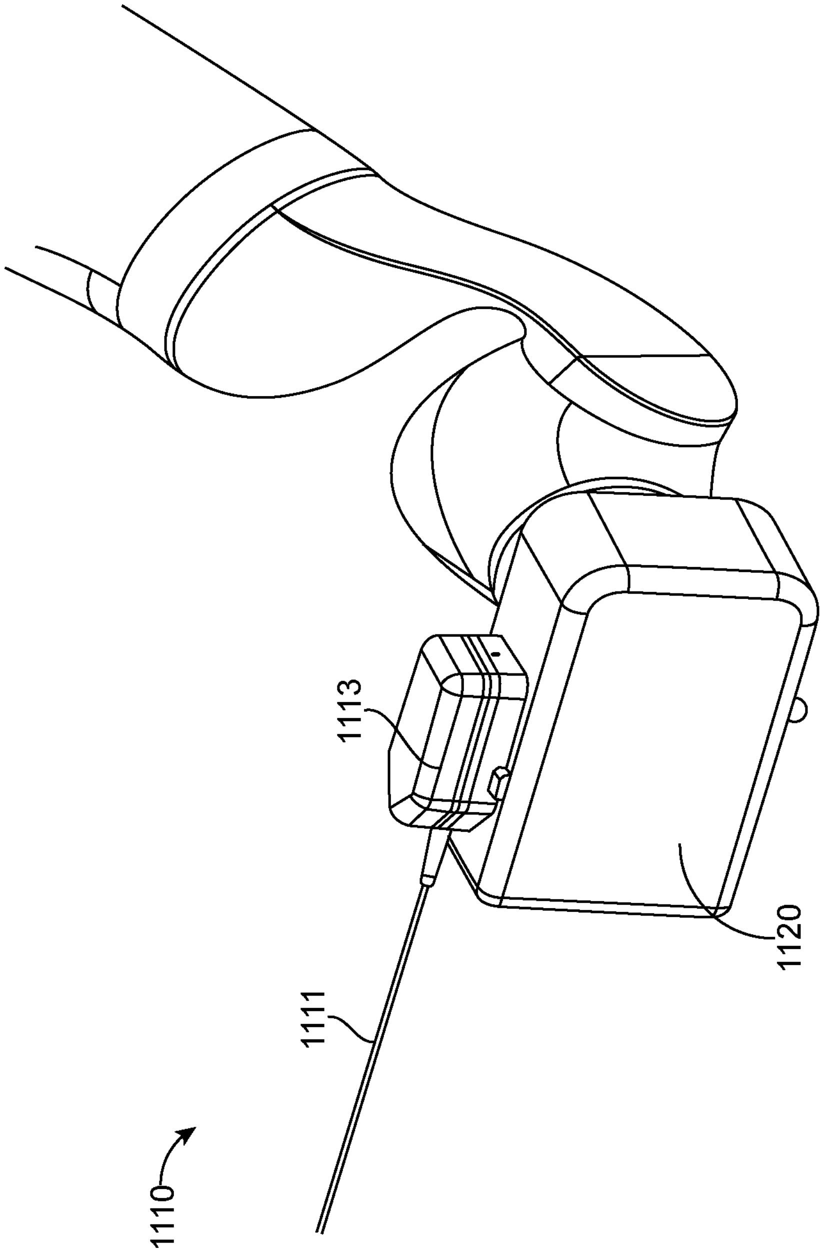
FIG. 11 shows an example of a robotic bronchoscope comprising a handle portion and a flexible elongate member.

As shown in FIG. 11, a robotic bronchoscope 1120 may comprise a handle portion 1113 and a flexible elongate member 1111. In some embodiments, the flexible elongate member 1111 may comprise a shaft, steerable tip, a steerable/active bending section and an anti-prolapse passive section. The robotic bronchoscope 1120 can be the same as the steerable catheter assembly as described in FIG. 10. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. In some cases, the bronchoscope may contain varying levels of stiffness along its shaft, as to improve functional operation. In some cases, a minimum bend radius along the shaft may vary so that the kink resistance or anti-prolapse capability may be configurable along the length.

The robotic bronchoscope can be releasably coupled to an instrument driving mechanism 1120. The instrument driving mechanism 1120 may be mounted to the arm of the robotic support system or to any actuated support system as described elsewhere herein. The instrument driving mechanism may provide mechanical and electrical interface to the robotic bronchoscope 1110. The mechanical interface may allow the robotic bronchoscope 1110 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

Figure 12:
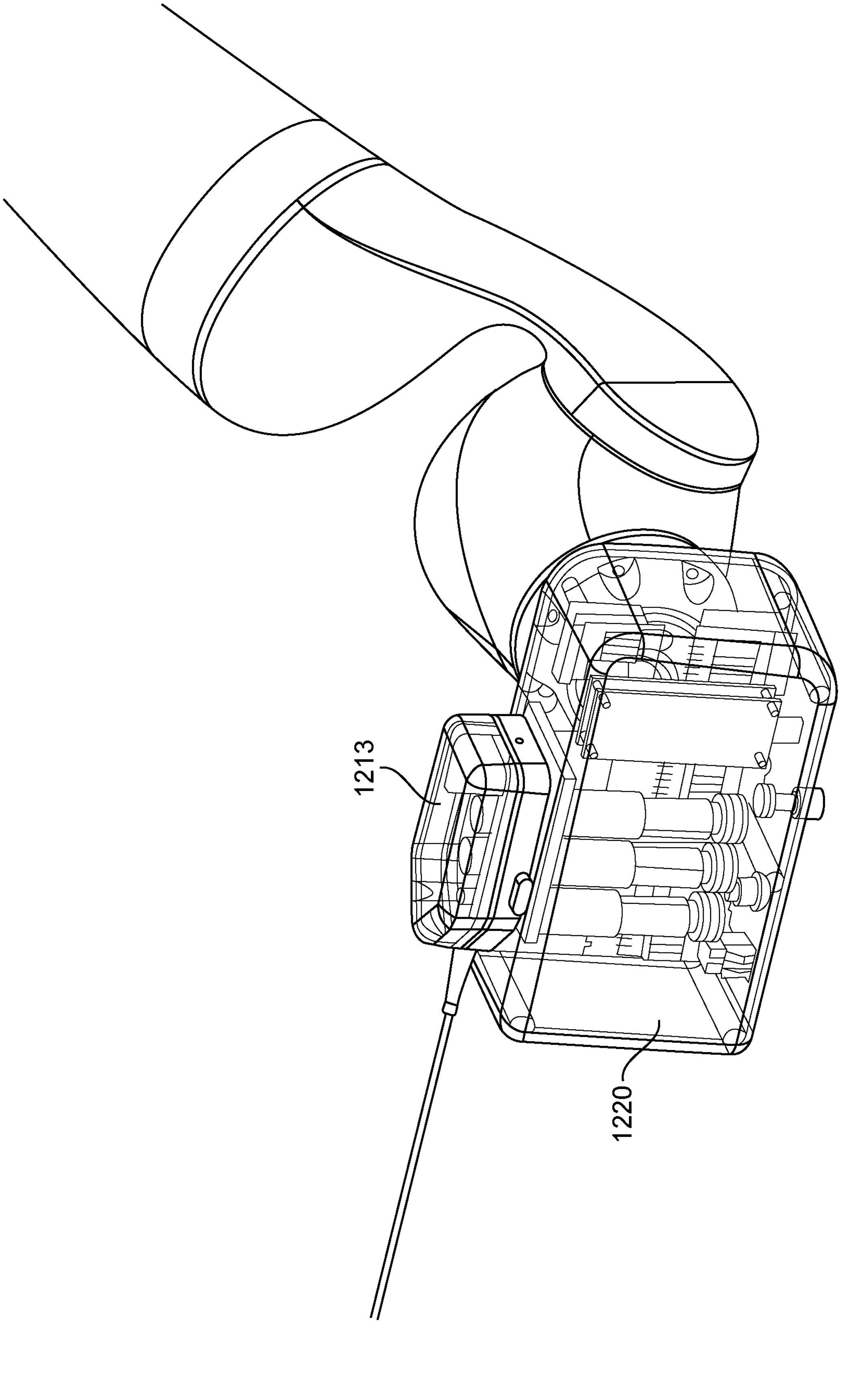
FIG. 12 shows an example of an instrument driving mechanism providing a mechanical interface to a handle portion of a robotic bronchoscope.

FIG. 12 shows an example of an instrument driving mechanism 1220 providing mechanical interface to the handle portion 1213 of the robotic bronchoscope. As shown in the example, the instrument driving mechanism 1220 may comprise a set of motors that are actuated to rotationally drive a set of pull wires of the flexible endoscope or catheter. The handle portion 1213 of the catheter assembly may be mounted onto the instrument drive mechanism so that its pulley assemblies or capstans are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive, adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

Figure 13:
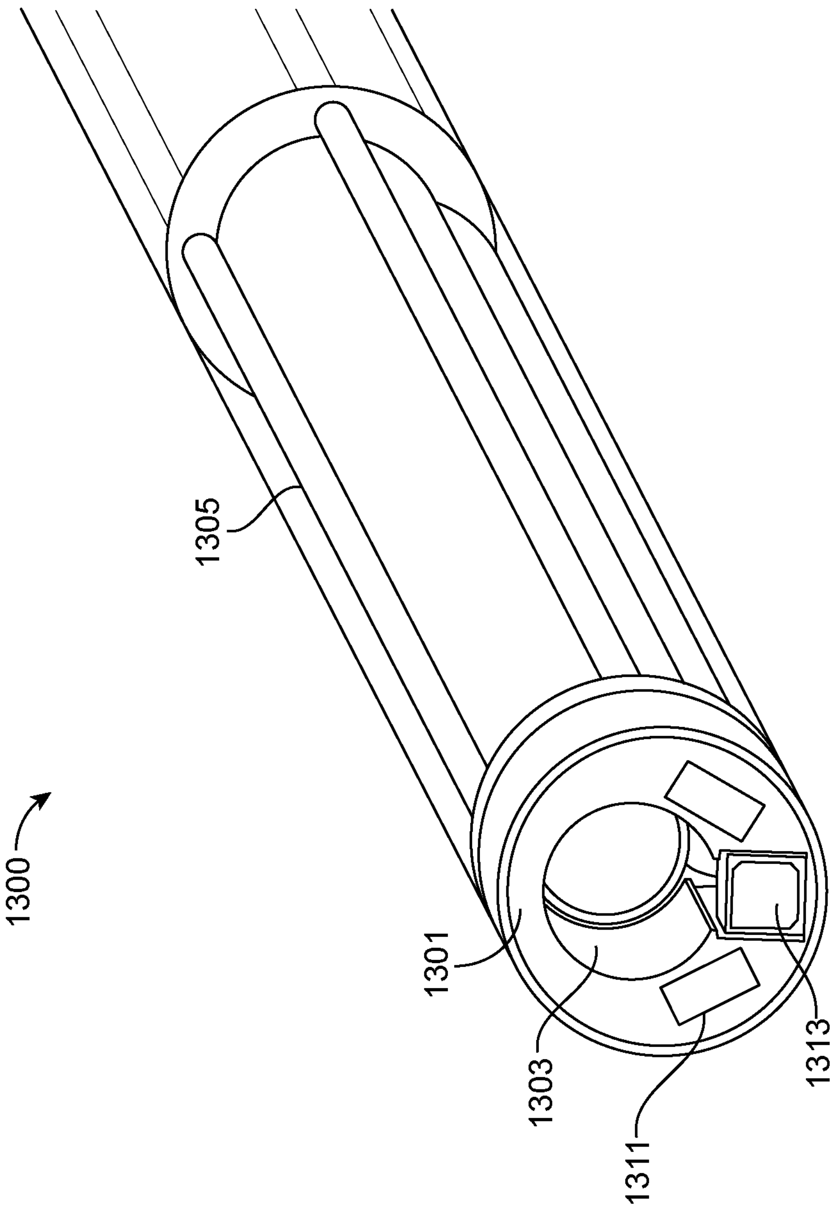
FIG. 13 shows an example of a distal tip of an endoscope.

FIG. 13 shows an example of a distal tip 1300 of an endoscope. In some cases, the distal portion or tip of the catheter 1300 may be substantially flexible such that it can be steered into one or more directions (e.g., pitch, yaw). The catheter may comprise a tip portion, bending section, and insertion shaft. In some embodiments, the catheter may have variable bending stiffness along the longitudinal axis direction. For instance, the catheter may comprise multiple sections having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some embodiments, the catheter may have variable minimum bend radius along the longitudinal axis direction. The selection of different minimum bend radius at different location long the catheter may beneficially provide anti-prolapse capability while still allow the catheter to reach hard-to-reach regions. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1305. The distal portion of the catheter may be made of any suitable material such as co-polymers, polymers, metals or alloys such that it can be bent by the pull wires. In some embodiments, the proximal end or terminal end of one or more pull wires 1305 may be coupled to a driving mechanism (e.g., gears, pulleys, capstan etc.) via the anchoring mechanism as described above.

The pull wire 1305 may be a metallic wire, cable or thread, or it may be a polymeric wire, cable or thread. The pull wire 1305 can also be made of natural or organic materials or fibers. The pull wire 1305 can be any type of suitable wire, cable or thread capable of supporting various kinds of loads without deformation, significant deformation, or breakage. The distal end or portion of one or more pull wires 1305 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The catheter may have a dimension so that one or more electronic components can be integrated to the catheter. For example, the outer diameter of the distal tip may be around 4 to 4.4 millimeters (mm), and the diameter of the working channel 1303 may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1313. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1311 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

Figure 14:
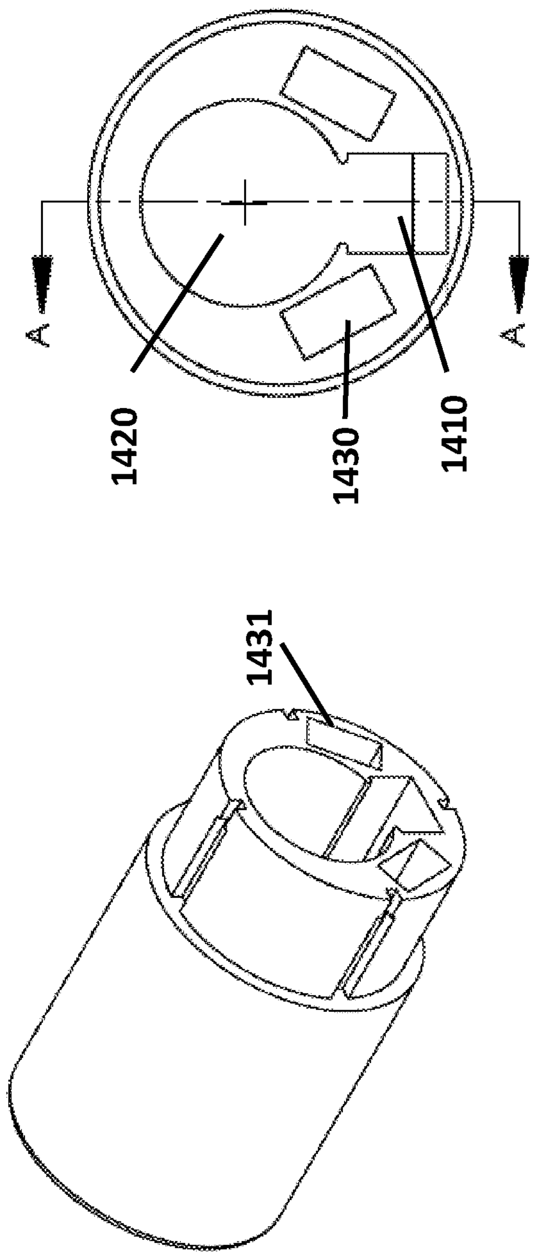
FIG. 14 shows an example distal portion of the catheter with integrated imaging device and the illumination device.

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 14 shows an example distal portion of the catheter with integrated imaging device and the illumination device. A camera may be located at the distal portion. The distal tip may have a structure to receive the camera, illumination device and/or the location sensor. For example, the camera may be embedded into a cavity 1410 at the distal tip of the catheter. The cavity 1410 may be integrally formed with the distal portion of the cavity and may have a dimension matching a length/width of the camera such that the camera may not move relative to the catheter. The camera may be adjacent to the working channel 1420 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1430 having a dimension matching a dimension of the miniaturized LED light source. As shown in the illustrated example, two cavities 1430 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1431 may be placed at the forwarding end face of the distal tip providing precise positioning of the LEDs as well as sufficient room for the glue. The cover 1431 may be composed of transparent material matching the refractive index of the glue so that the illumination light may not be obstructed.

The working channel (e.g., working channel 1303, 1420) may be designed to provide protection for the internal components such as flexible instruments (e.g., needle, forceps, etc.). When flexible instruments pass through a conventional working channel, they may be obstructed by the working channel due to kinking, ovalizing and/or high friction force. The working channel herein may advantageously address the above drawbacks by providing a high hoop strength and a capability of achieving low bend radius. The working channel may also be designed to provide low friction in the inner surface.

Figure 15:
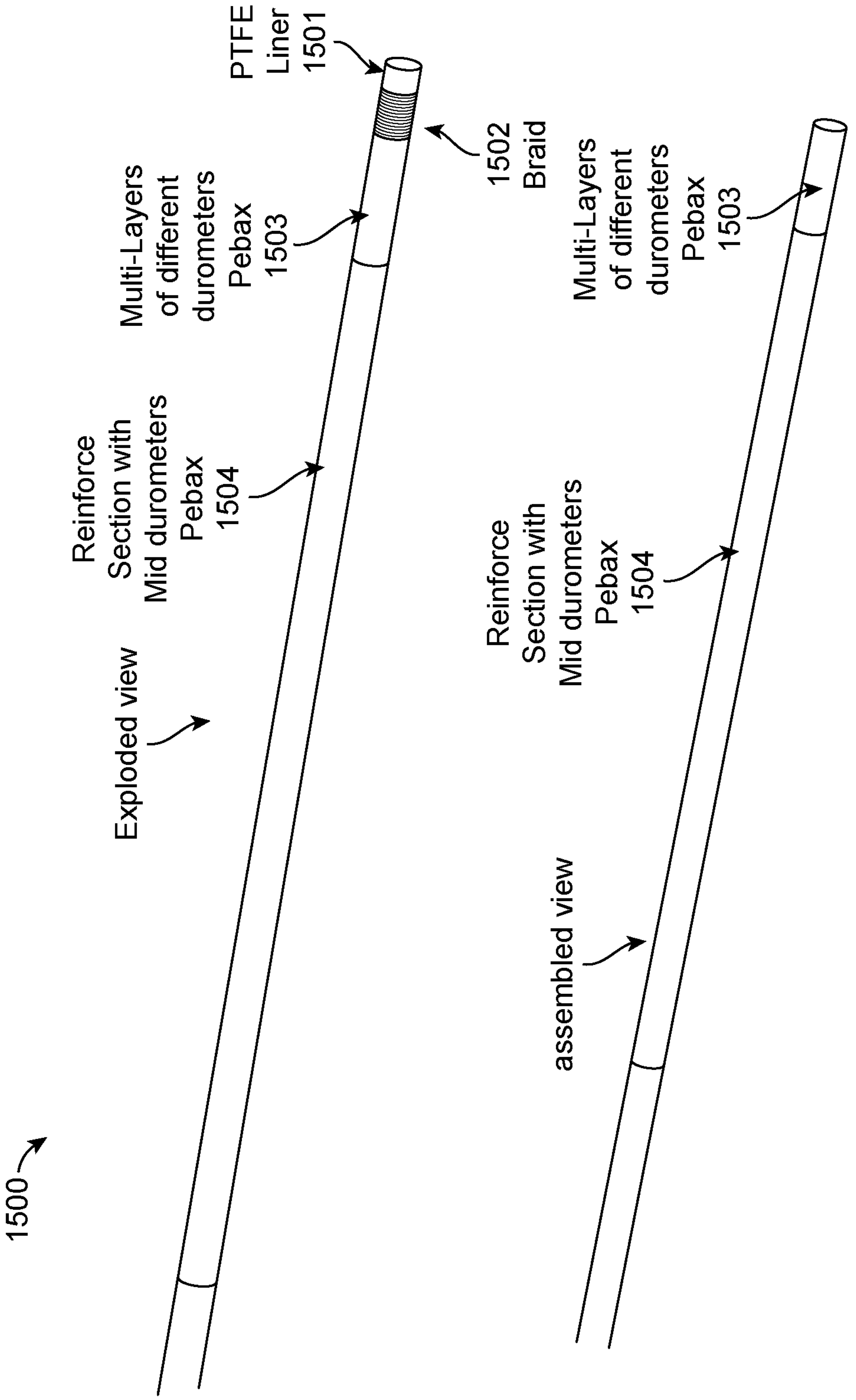
FIG. 15 shows an example of a working channel.

The working channel herein may comprise various stiffness along the length to provide flexibility of achieving a small bend radius while having a high hoop strength (e.g., high capability to bear force over area exerted circumferentially (perpendicular to the axis and the radius) in both directions in the cylinder wall) thereby providing sufficient protection for the internal components. In some embodiments, the working channel may comprise a plurality of segments. FIG. 15 shows an example of a working channel 1500. In some embodiments, the working channel may comprise multiple layers and/or multiple segments. As illustrated in the exploded view, the working channel 1500 may comprise an inner layer 1501 throughout the length of the working channel. The inner layer 1501 may be formed of a polymer such as PTFE material. The inner layer or the PTFE liner 1501 may provide a low friction inner surface to the internal components. The working channel may comprise a second layer 1502 coming outside of the PTFE liner. In some embodiments, the second layer 1502 may be formed of stainless steel braid with optimal pitch to provide desired stiffness. For example, the stainless steel braid with 150 Pitch Per Inch (PPI)+/−30 PPI (Full Pattern) may be used to provide high hoop strength to the entire working channel 1500. This beneficially strengthens the working channel and prevents it from kinking. The working channel may comprise an outer layer 1503. The outer layer may be formed of mid stiffness and high stiffness Pebax to cover the entire working channel. In some cases, additional layer may be included to reinforce a selected segment. For example, a mid stiffness Pebax segment 1504 may be used to provide an additional hoop strength to a selected segment of working channel thereby reinforcing the segment. This may beneficially allow for a small bending radius that is no greater than, 5 mm, 6 mm, 7 mm, 8 mm, 9 mm, 10 mm, 15 mm, 20 mm, or 30 mm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An articulating flexible endoscope comprising:

an elongated member extending between a distal end and a proximal end, the elongated member comprising:

an active bending section steerable by one or more pull wires; and a passive section located between the active bending section and a proximal shaft section, wherein the passive section comprises an anti-prolapse structure that determines a minimum bend radius of the passive section thereby preventing prolapse, wherein the anti-prolapse structure comprises a cut pattern integrally formed in a substantially tubular component of the passive section, and wherein the minimum bend radius of the passive section is reached when a plurality of gaps of the cut pattern close on an inner curve of the passive section thereby preventing the passive section from bending further.

2. The articulating flexible endoscope of claim 1, wherein the distal end is connected to a distal tip portion of the articulating flexible endoscope and wherein the distal tip portion comprises a structure to receive an imaging device, a position sensor, and an illumination device.

3. The articulating flexible endoscope of claim 1, wherein the proximal end is connected to a proximal portion of the articulating flexible endoscope and wherein the proximal portion comprises a driving mechanism for applying a force to the one or more pull wires.

4. The articulating flexible endoscope of claim 1, wherein the cut pattern comprises a gap and an interlocking feature.

5. The articulating flexible endoscope of claim 1, wherein the passive section has two or more different minimum bend radii.

6. The articulating flexible endoscope of claim 5, wherein the anti-prolapse structure comprises a cut pattern and wherein the two or more different minimum bend radii are determined by selecting different gap sizes and/or selecting different pitches of the cut pattern.

7. The articulating flexible endoscope of claim 1, wherein a minimum bend radius of the active bending section is smaller than the minimum bend radius of the passive section.

8. The articulating flexible endoscope of claim 7, wherein the active bending section has two or more different minimum bend radii.

9. The articulating flexible endoscope of claim 1, further comprising one or more coil pipes with a distal end anchored to an interface between the passive section and the active bending section.

10. The articulating flexible endoscope of claim 9, wherein a proximal end of the one or more coil pipes is anchored to a handle of the articulating flexible endoscope.

11. The articulating flexible endoscope of claim 1, further comprising a jacket as an outer layer of the elongated member.

12. The articulating flexible endoscope of claim 11, wherein the jacket comprises multiple layers and has variable stiffness along a length of the jacket.

13. The articulating flexible endoscope of claim 1, wherein the proximal shaft section has a stiffness greater than a stiffness of the passive section.

14. A method for preventing prolapse or kink for an articulating flexible endoscope, the method comprises:

providing an elongated member;

navigating the articulating flexible endoscope through a passageway by steering an active bending section of the elongated member via one or more pull wires; and providing a passive section located between the active bending section and a proximal shaft section, wherein the passive section comprises an anti-prolapse structure that determines a minimum bend radius of the passive section thereby preventing prolapse while the articulating flexible endoscope is navigating through the passageway, wherein the anti-prolapse structure comprises a cut pattern integrally formed in a substantially tubular component of the passive section, and wherein the minimum bend radius of the passive section is reached when a plurality of gaps of the cut pattern close on an inner curve of the passive section thereby preventing the passive section from bending further.

15. The method of claim 14, wherein the cut pattern comprises repeated gap feature and interlocking feature.

16. The method of claim 14, wherein the passive section has two or more different minimum bend radii.

* * * * *